United States Patent [19]

Schmid

[11] 4,333,931
[45] Jun. 8, 1982

[54] METHOD OF COMBATTING HARMFUL MICROORGANISMS USING QUINOXALINE COMPOUNDS

[75] Inventor: Wolfgang Schmid, Therwil, Switzerland

[73] Assignee: Ciba-Geigy Corporation, Ardsley, N.Y.

[21] Appl. No.: 221,181

[22] Filed: Dec. 29, 1980

Related U.S. Application Data

[62] Division of Ser. No. 102,281, Dec. 10, 1979, Pat. No. 4,254,120.

[30] Foreign Application Priority Data

Dec. 19, 1978 [CH] Switzerland .................. 12887/78
Jul. 5, 1979 [CH] Switzerland .................... 6295/79
Nov. 20, 1979 [CH] Switzerland .................. 10341/79

[51] Int. Cl.³ .............. A61K 31/535; A61K 31/495
[52] U.S. Cl. ........................... 424/248.54; 424/250
[58] Field of Search ................ 424/248.52, 248.54, 424/250

[56] References Cited

FOREIGN PATENT DOCUMENTS 1308370 2/1973 United Kingdom .

Primary Examiner—Robert W. Ramsuer
Attorney, Agent, or Firm—Frederick H. Rabin

[57] ABSTRACT

Novel quinoxaline-di-N-oxide derivatives of the general formula

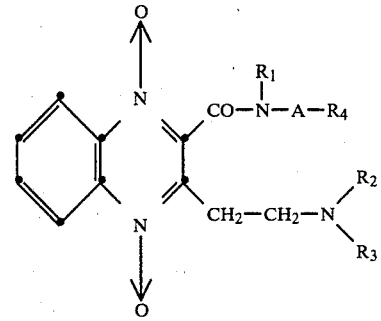

in which $R_1$ is hydrogen or straight-chain or branched-chain alkyl having 1 to 4 carbon atoms, $R_2$ and $R_3$ independently of one another are each straight-chain or branched-chain alkyl having 1 to 4 carbon atoms, or together with the N atom they form a heterocyclic ring which is unsubstituted or is substituted by alkyl having 1 to 4 carbon atoms, and which has 4 to 5 ring carbon atoms and optionally an oxygen atom as further hetero atom, $R_4$ is hydrogen, methoxy, methylthio, hydroxyl, fluorine, chlorine, bromine or cyano, A is alkylene having 1 to 4 carbon atoms, with the proviso that if $R_4$ has a meaning other than cyano, A is 1,2-ethylene, and $R_1$ is hydrogen, including the acid addition salts thereof; processes for producing them; compositions containing these compounds; and the use thereof. The novel active substances serve to combat pathogenic microorganisms in the field of veterinary medicine. They are effective in the case of diseases of the respiratory tract in poultry, and infections of the intestinal tract and of the urogenital system in domestic animals and productive livestock. They are in addition suitable as a feed additive for promoting the growth of animals. Depending on the type of application, the novel active substances may be administered perorally or via the abomasum or directly by injection, the active substances being applied on their own or in combination with customary inert carriers, either in the solid form or in the liquid form.

7 Claims, No Drawings

METHOD OF COMBATTING HARMFUL MICROORGANISMS USING QUINOXALINE COMPOUNDS

This is a divisional of application Ser. No. 102,281 filed on Dec. 10, 1979, now U.S. Pat. No. 4,254,120.

The present invention relates to novel quinoxaline-di-N-oxide derivatives, to processes for producing them, to compositions containing the novel compounds, and to the use thereof for combating pathogenic microorganisms, and also as a feed additive for domestic animals and for productive livestock.

The novel quinoxaline-di-N-oxide derivatives correspond to the general formula I

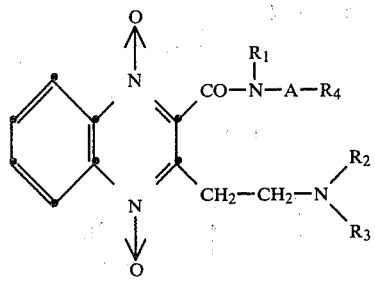

in which
$R_1$ is hydrogen or straight-chain or branched-chain alkyl having 1 to 4 carbon atoms,
$R_2$ and $R_3$ independently of one another are each straight-chain or branched-chain alkyl having 1 to 4 carbon atoms, or together with the N atom they form a heterocyclic ring which is unsubstituted or is subsituted by alkyl having 1 to 4 carbon atoms, and which has 4 to 5 ring carbon atoms and optionally an oxygen atom as further hetero atom,
$R_4$ is hydrogen, methoxy, methylthio, hydroxyl, fluorine, chlorine, bromine or cyano,
A is alkylene having 1 to 4 carbon atoms, with the proviso that if $R_4$ has a meaning other than cyano, A is 1,2-ethylene, and $R_1$ is hydrogen,
and include the acid addition salts thereof.

By alkyl are meant methyl, ethyl and the isomers of the propyl group and of the butyl group.

To be mentioned as examples of the acid anions of the acid addition salts are: acetate, citrate, maleate, lactate, furmarate, pamoate, tosylate, bromide and preferably chloride, and also salts with ion exchangers, for example Amberlist 15.

Substances which are structurally similar to the compounds of the formula I according to the invention are already known from the German Offenlegungsschriften Nos. 1,670,935 and 1,620,114, and from the British Patent Specification No. 1,223,720. For combating pathogenic microorganisms, the compounds of the formulae I and Ia according to the invention are distinctly superior to the known compounds, and compared with these known compounds they are characterised by a more pronounced therapeutic activity and also by low toxicity. Furthermore, they are in an advantageous manner readily soluble both in water and in organic solvents.

The compounds of the formula I according to the invention have a good microbicidal action, and are suitable for combating pathogenic microorganisms in the field of veterinary medicine. They are distinguished by a good action against diseases of the respiratory tract caused by E. coli in poultry. The novel compounds of the invention are in addition suitable for controlling infections of the intestinal tract, for example diarrhoea in pigs, and also infections of the urogenital system.

The novel compounds also have good properties for promoting the growth of domestic animals, and of productive livestock, such as pigs, poultry and ruminants.

Compounds which are distinguished by high effectiveness with regard to their properties as substances which promote animal growth and which at the same time have low toxicity are in particular the compounds of the formula Ib

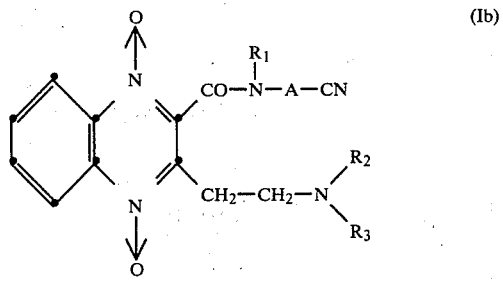

in which $R_1$ is hydrogen or $C_1$-$C_4$-alkyl, and $R_2$ and $R_3$ independently of one another are each $C_1$-$C_4$-alkyl, or together with the N atom they form a heterocyclic ring which is unsubstituted or is substituted by $C_1$-$C_4$-alkyl, and which has 4 to 5 ring carbon atoms and optionally an oxygen atom as further hetero atom, and the acid addition salts of these compounds.

Among the compounds of the formula Ib, the following are to be mentioned as compounds having particularly favourable toxicity values in the case of pigs and poultry:

TABLE 1

Compound

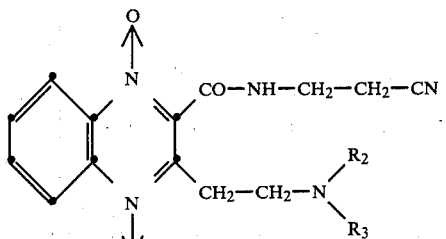

or

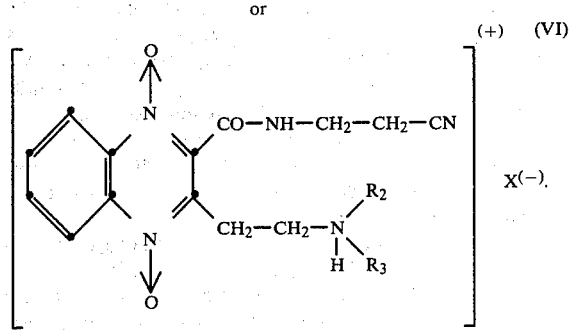

| Comp. No. | 1 | 2 | 3 | 4 | 5 |
|---|---|---|---|---|---|
| $R_2$: | ⟨ ⟩ | $CH_3$ | ⟨ ⟩ | ⟨O⟩ | $C_2H_5$ |
| $R_3$: | ⟨ ⟩ | $CH_3$ | ⟨ ⟩ | ⟨ ⟩ | $C_2H_5$ |

TABLE 1-continued

Compound

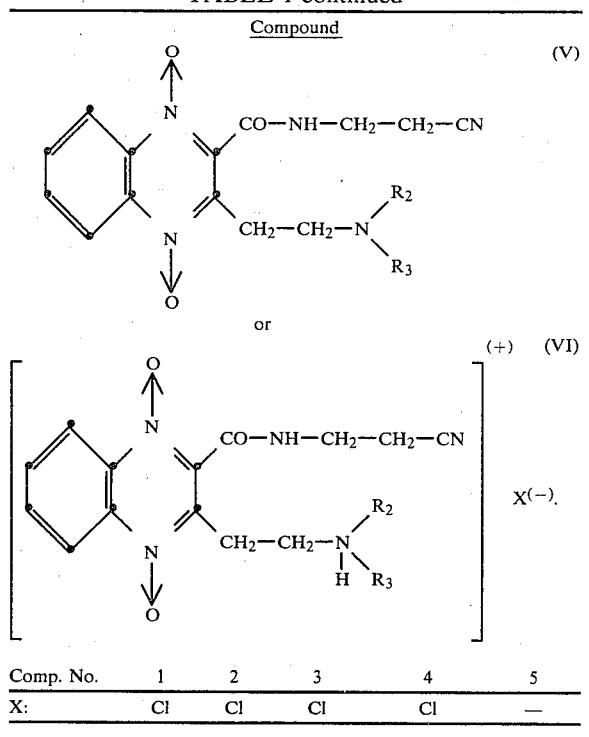

| Comp. No. | 1 | 2 | 3 | 4 | 5 |
|---|---|---|---|---|---|
| X: | Cl | Cl | Cl | Cl | — |

A further compound likewise having a good action in promoting growth and having low toxicity is the following:

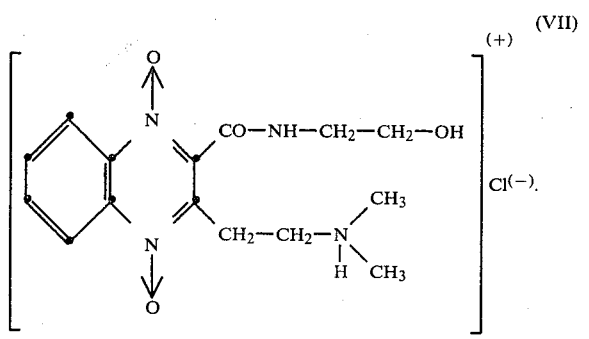

Depending on the intended use, the active substances according to the invention may be administered to the animals perorally or via the abomasum or directly by injection into the animals, in single doses or in repeated doses, the active substances being applied, on their own or in combination with inert carriers and/or diluents, in the form of solutions, emulsions, suspensions, powders, tablets, boluses and capsules. The active substances or mixtures containing them can also be added to the feed or to the drinking water, or they can be contained in so-called feed permixes.

The good therapeutic activity of the compounds of the formulae I and Ia was able to be verified both in vitro and, in particular, on the animal, after either oral or subcutaneous application, in the case of acute bacterial infections. The sphere of action of the said compounds embraces both gram-positive and gram-negative bacteria.

The compounds of the formula I can be produced, using known methods, from 1,4-dioxido-3-methyl-quinoxaline-(2)-carboxylic acid amides [see Organic Reactions, Vol. I (1942) 312] in the following manner:

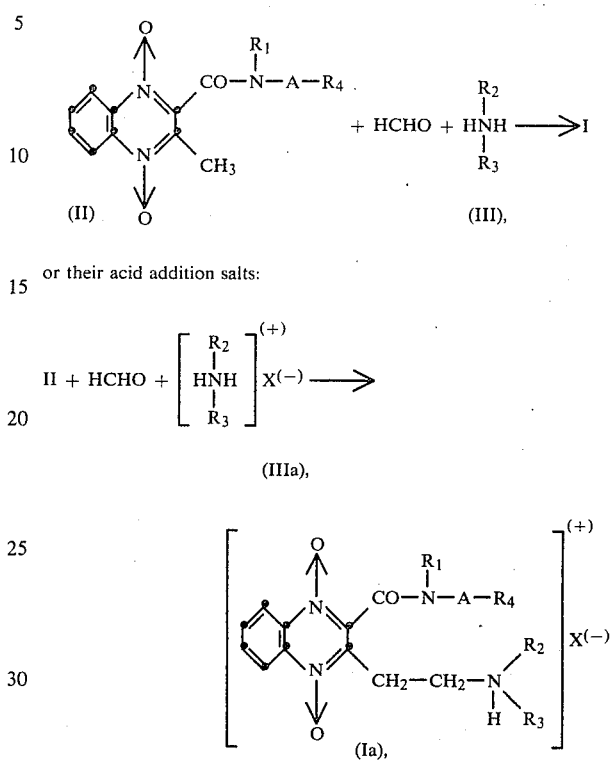

or their acid addition salts:

and the salts of the formula Ia can be converted into the free compounds of the formula I as follows:

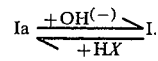

In the given formulae, the radicals $R_1$ to $R_4$ have the meanings initially given under the formula I, and X is the anion of an inorganic or organic acid.

The reaction is carried out in organic solvents inert to the reactants, for example formamide, N-methylformamide, dimethylformamide, dimethylsulfoxide, tetrahydrofuran, dioxane, toluene, propionitrile, butyronitrile, benzonitrile, methyl cellosolve or preferably acetonitrile.

The reaction is performed at temperatures of 20° to 150° C., preferably 40° to 80° C.

Some of the starting materials of the formula II used to produce the compounds of the formula I according to the invention have already been described (see German Offenlegungsschriften Nos. 1,670,935 and 2,111,710, British Patent Specification No. 1,308,370, and Swiss Patent Application No. 7718/77). When $R_4$ in formula II is fluorine, the corresponding compound can be produced by a process given in the aforementioned descriptions. In the case where $R_4$ is bromine, $R_1$ is hydrogen and A is ethylene (see formula II'), the following new production process is used:

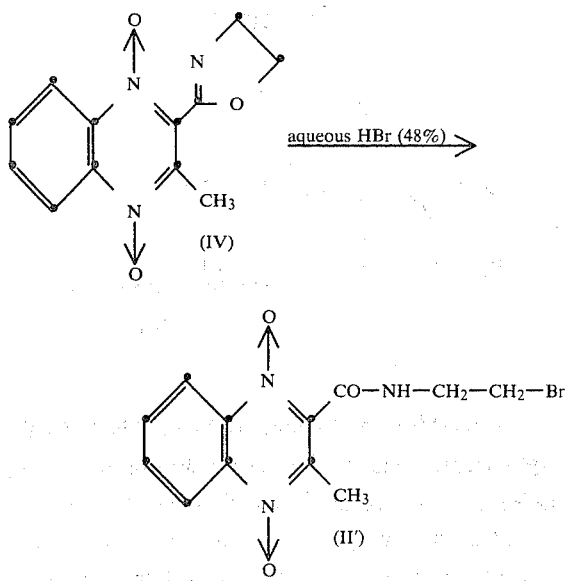

When R$_4$ is chlorine, the corresponding compound of the formula II″ (Cl in place of Br in formula II′), which has already been mentioned in German Offenlegungsschrift No. 2,111,710, can be produced likewise using the abovedescribed process by reaction of 2-[oxazolinyl(2′)]-3-methyl-quinoxaline-1,4-di-N-oxide (German Offenlegungsschrift No. 2,111,710, Example 21) with concentrated aqueous hydrochloric acid.

Also known are the secondary amines, and their acid addition salts, used as starting materials of the formula III and IIIa, of which are to be mentioned as examples: dimethylamine, diethylamine, di-n-propylamine, di-isopropylamine, di-n-butylamine, pyrrolidine, piperidine and morpholine, and also acid addition salts thereof.

The formaldehyde used in the process for producing the compounds of the formulae I and Ia can be employed either in the form of an aqueous solution or in the form of solid agents splitting off formaldehyde, for example paraformaldehyde.

EXAMPLE 1

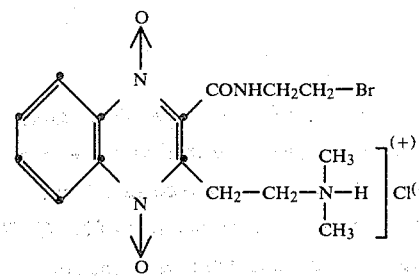

(a) 49 g (0.2 mol) of 2-[oxazolinyl(2′)]-3-methyl-quinoxaline-1.4-di-N-oxide is added to 200 ml of 48% aqueous hydrobromic acid, and the mixture is subsequently stirred for one further hour at room temperature. 500 g of ice is added to this mixture, and a colourless crystalline product precipitates; it is then filtered off, and dried at room temperature over phosphorus pentoxide. The yield is 63.1 g (96.7%) of 1,4-dioxido-3-methyl-quinoxaline(2)-N-(2′-bromoethyl)-carboxylic acid amide, which melts at 165° C. with decomposition.

(b) 24.5 g (0.075 mol) of 1.4-dioxido-3-methyl-quinoxaline(2)-N-(2′-bromoethyl)-carboxylic acid amide, 2.3 g of paraformaldehyde and 6 g of dimethylamine hydrochloride are placed together with 180 ml of acetonitrile into the reaction vessel, and the whole is heated in an oil bath at 100° C. The suspension gradually turns into a clear solution, which is held, with stirring, for a further 20 hours at the same temperature. The solution is subsequently cooled to 10° C., and a product crystallises out. The mixture is then heated to 60° C., and afterwards filtered. The yield is 14.6 g (46.5%) of 1.4-dioxido-3-(2′-dimethylaminoethyl)-quinoxaline(2)-N-(2″-bromoethyl)-carboxylic acid amide hydrochloride, which melts at 164°–166° C. with decomposition.

EXAMPLE 2

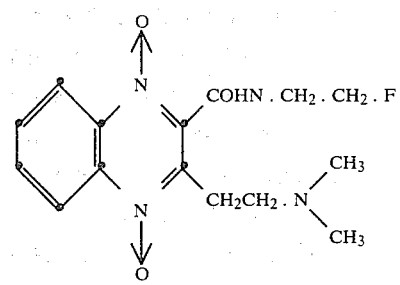

(a) 2.2 g of n-butylamine is added dropwise, during 10 minutes, to a suspension of 4.4 g (0.03 mol) of N-2-fluoroethylacetoacetic acid amide and 4 g of benzofuroxane in 30 ml of methanol, in the course of which the temperature rises to 35° C., and for a short time there is formed a clear dark-coloured solution. Stirring is continued at the same temperature in the water bath; the temperature is lowered after 10 hours to 20° C.; the crystalline product which has precipitated is filtered off with suction, and is washed with a small amount of cold methanol; the product is recrystallised from methanol to yield 6 g (75.9%) of pure crystalline 1.4-dioxido-3-methyl-quinoxaline-(2)-N-(2′-fluoroethyl)-carboxylic acid amide, which melts at 200°–202° C.

(b) 52.4 g (0.2 mol) of 1.4-dioxido-3-methyl-quinoxaline (2)-N-(2′-fluoroethyl)-carboxylic acid amide, 6 g of paraformaldehyde and 16 g of dimethylamine hydrochloride in 500 ml of acetonitrile are heated in an oil-bath at 100° C. The suspension gradually becomes a clear solution, which is maintained at the same temperature, with stirring, for a further 20 hours, with a crystalline product slowly commencing to crystallise out after 10 hours. This is filtered off from the warm mixture, and is recrystallised from ethanol to thus obtain 45.6 g (63.7%) of 1.4-dioxido-3-(2′-dimethylaminoethyl)-quinoxaline(2)-N-(2′-fluoroethyl)-carboxylic acid amide hydrochloride, which melts at 182°–184° C. with decomposition.

(c) 3.6 g (0.01 mol) of 1.4-dioxido-3-(2′-dimethylaminoethyl)-quinoxaline(2)-N-(2″-fluoroethyl)-carboxylic acid amide hydrochloride is dissolved in a mixture of 30 ml of water and 30 ml of methylene chloride; to this mixture is then added, with stirring, 10 ml of 1 N sodium hydroxide solution, and the methylene chloride phase is immediately separated. There is obtained from the solution, dried over sodium sulfate, 2.7 g (84.4%) of pure crystalline 1.4-dioxido-3-(2′-dimethylaminoethyl)-quinoxaline(2)-N-(2″-fluoroethyl)-carboxylic acid amide, m.p. 166°–167° C.

EXAMPLE 3

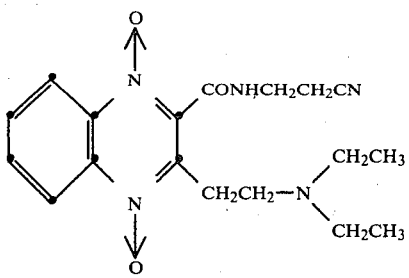

27.2 g (0.1 mol) of 1,4-dioxido-3-methyl-quinoxaline(2)-N-(2'-cyanoethyl)-carboxylic acid amide is suspended with 20 g (0.2 mol) of 30% aqueous formaldehyde solution and 14.6 g (0.2 mol) of diethylamine in 250 ml of acetonitrile. Stirring is subsequently maintained for 16 hours at 40° C., and the clear solution formed is concentrated by evaporation. After the addition of methanol to the oily residue, there is precipitated from the clear dark-brown-coloured solution 23.4 g (65.5%) of 1,4-dioxido-3-(2'-diethylaminoethyl)-quinoxaline(2)-N-(2'-cyanoethyl)-carboxylic acid amide in the form of deep-yellow crystals, which melt at 159°–160° C. with decomposition.

EXAMPLE 4

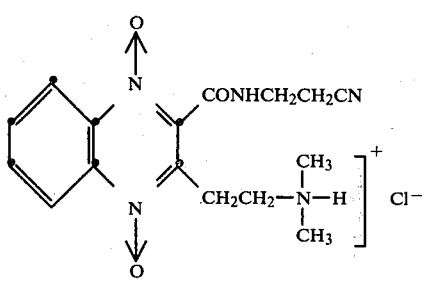

13.6 g (0.05 mol) of 1,4-dioxido-3-methyl-quinoxaline(2)-N-(2'-cyanoethyl)-carboxylic acid amide is suspended with 10 g (0.1 mol) of 30% aqueous formaldehyde solution and 8.1 g (0.1 mol) of dimethylamine hydrochloride in 200 ml of acetonitrile. The suspension is subsequently stirred under reflux for 24 hours, and 13.6 g (74.3%) of yellowish-white crystals of 1.4-dioxido-3-(2'-dimethylaminoethyl)-quinoxaline(2)-(2'-cyanoethyl)-carboxylic acid amide hydrochloride is then filtered off hot; the crystals melt at 211°–213° C. with decomposition.

EXAMPLE 5

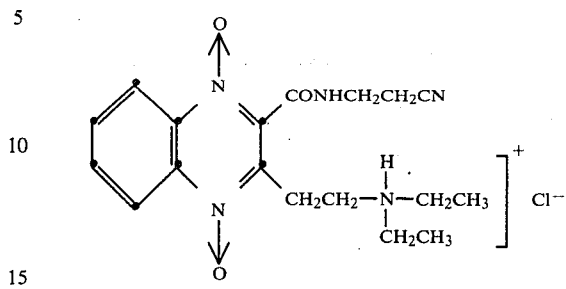

17.8 g (0.05 mol) of 1,4-dioxido-3-(2'-diethylaminoethyl)-quinoxaline(2)-N-(2'-cyanoethyl)-carboxylic acid amide is suspended in 50 ml of water, and then dissolved, with cooling, at 20° C. in 50 ml of 1 N hydrochloric acid. The clear light-coloured solution is evaporated to dryness; residual moisture is removed by drying over phosphorus pentoxide. The highly viscous residue is recrystallised from isopropanol/acetone to yield 12.5 g (63.6%) of 1,4-dioxido-3-(2'-diethylaminoethyl)-quinoxaline(2)-n-(2'-cyanoethyl)-carboxylic acid amide hydrochloride in the form of yellowish-white crystals, which melt at 180°–181° C.

EXAMPLE 6

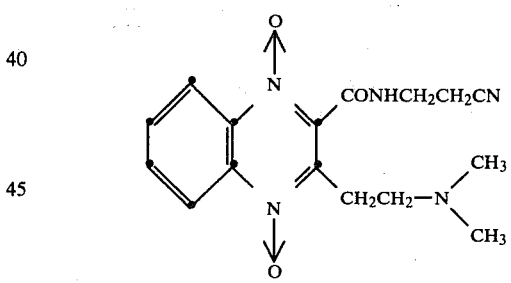

18.2 g (0.05 mol) of 1,4-dioxido-3-(2'-dimethylaminoethyl)-quinoxaline(2)-(2'-cyanoethyl)-carboxylic acid amide hydrochloride is dissolved in 100 ml of water. There is then added, at a temperature of 20° C., 50 ml of 1 N sodium hydroxide solution, and the solution is extracted with methylene chloride. From the methylene chloride phase, dried over sodium sulfate, is obtained 15.6 g (95%) of 1,4-dioxido-3-(2'-dimethylaminoethyl)-quinoxaline(2)-(2'-cyanoethyl)-carboxylic acid amide, which melts at 161° C. with decomposition.

The following compounds were produced or are producible by processes analogous to those described in the Examples:

TABLE 2

Compound

[Structures shown: two forms — neutral and cationic salt — of a dinitroso benzene derivative with CO-N(R₁)-A-R₄ and CH₂-CH₂-N(R₂)(R₃) substituents, with counterion X(−)]

| No. | A | R₁ | R₂ | R₃ | R₄ | X | m.p. in °C. |
|---|---|---|---|---|---|---|---|
| 1 | CH₂ | H | CH₃ | CH₃ | CN | Cl | 179–181 |
| 2 | CH₂ | H | CH₃CH₂ | CH₃CH₂ | CN | — | 156–157 |
| 3 | CH₂ | H | CH₃CH₂ | CH₃CH₂ | CN | Cl | |
| 4 | CH₂—CH₂ | H | CH₃(CH₂)₂ | CH₃(CH₂)₂ | CN | — | 128–130 |
| 5 | CH₂—CH₂ | H | CH₃(CH₂)₃ | CH₃(CH₂)₃ | CN | — | 130–132 |
| 6 | CH₂—CH₂ | H | (pyrrolidine ring) | | CN | — | 160–161 |
| 7 | CH₂—CH₂ | H | (piperidine ring) | | CN | — | 160–161 |
| 8 | CH—CH₂ \| CH₃ | H | CH₃ | CH₃ | CN | Cl | |
| 9 | CH—CH₂ \| CH₃ | H | CH₃CH₂ | CH₃CH₂ | CN | — | 136–138 |
| 10 | CH—CH₂ \| CH₃ | H | CH₃CH₂ | CH₃CH₂ | CN | Cl | |
| 11 | CH₂ | H | CH₃ | CH₃ | CN | Br | 158–160 |
| 12 | CH₂—CH₂ | H | CH₃ | CH₃ | CN | — | 158–160 |
| 13 | CH₂—CH₂ | H | CH₃ | CH₃ | CN | Br | 202 (decomp.) |
| 14 | CH₂—CH₂ | H | (pyrrolidine ring) | | CN | Cl | 187–189 |
| 15 | CH₂—CH₂ | H | CH₃ | CH₃ | CN | Cl | 211–213 |
| 16 | CH₂—CH₂ | H | CH₃ | CH₃ | CN | Amberlist 15 | > 300 |
| 17 | CH₂—CH₂ | H | CH₃—CH₂ | CH₃—CH₂ | CN | — | 158–159 |
| 18 | CH₂—CH₂ | H | CH₃—CH₂ | CH₃—CH₂ | CN | Cl | 180–181 |
| 19 | CH₂—CH₂ | H | CH₃—CH₂ | CH₃—CH₂ | CN | Amberlist 15 | > 300 |
| 20 | CH₂—CH₂ | H | (piperidine ring) | | CN | Cl | 190–192 |
| 21 | CH₂—CH₂ | H | (morpholine ring) | | CN | Cl | 192 |
| 22 | CH₂—CH₂ | H | CH₃ | CH₃ | OH | Cl | 159–160 (decomp) |
| 23 | CH₂—CH₂ | H | CH₃ | CH₃ | S—CH₃ | Cl | 185–186 |
| 24 | CH₂—CH₂ | H | CH₃ | CH₃ | S—CH₃ | — | 138–139 |
| 25 | CH₂—CH₂ | H | CH₃ | CH₃ | OCH₃ | Cl | 196–197 |
| 26 | CH₂—CH₂ | H | CH₃ | CH₃ | OCH₃ | — | 150–152 |
| 27 | CH₂—CH₂ | H | CH₃ | CH₃ | Br | Cl | 164–166 |
| 28 | CH₂—CH₂ | H | CH₃ | CH₃ | Cl | Cl | 194–196 (decomp) |
| 29 | CH₂—CH₂ | H | CH₃ | CH₃ | Cl | — | 139–140 |
| 30 | CH₂—CH₂ | H | (pyrrolidine ring) | | F | Cl | 182–183 (decomp) |
| 31 | CH₂—CH₂ | H | (piperidine ring) | | F | — | 174–175 |
| 32 | CH₂—CH₂ | H | CH₃ | CH₃ | H | Cl | 183–185 (decomp) |
| 33 | CH₂—CH₂ | H | CH₃ | CH₃ | H | — | 153–155 |

TABLE 2-continued

Compound

| No. | A | R₁ | R₂ | R₃ | R₄ | X | m.p. in °C. |
|---|---|---|---|---|---|---|---|
| 34 | CH₂—CH₂ | H | \multicolumn{2}{c}{(dioxane ring)} | H | Cl | 188–190 (decomp) |
| 35 | CH₂—CH₂ | H | \multicolumn{2}{c}{(dioxane ring)} | H | — | 185–186 |
| 36 | CH₂—CH₂ | H | CH₃ | CH₃ | F | Cl | 182 |
| 37 | CH₂—CH₂ | H | CH₃ | CH₃ | F | — | 166–167 |

EXAMPLE 7

For producing final feed containing as active substance a compound of the formula I or an acid addition salt thereof (formula Ia) at a concentration of (a) 25 ppm, (b) 50 ppm, (c) 200 ppm and (d) 400 ppm, there are prepared the following feed premixes:

(a)

0.15 part by weight of one of the compounds according to formula I or Ia,
49.85 parts by weight of bolus alba,
150.0 parts by weight of standard feed for poultry, pigs or ruminants, (b)

0.30 part by weight of one of the compounds according to formula I or Ia,
44.70 parts by weight of bolus alba,
5.0 parts by weight of silicic acid,
150.0 parts by weight of standard feed for poultry, pigs or ruminants, (c)

1.2 parts by weight of one of the compounds according to formula I or Ia,
43.8 parts by weight of bolus alba,
5.0 parts by weight of silicic acid,
150.0 parts by weight of standard feed for poultry, pigs or ruminants, (d)

2.4 parts by weight of one of the compounds according to formula I or Ia,
47.6 parts by weight of bolus alba,
150.0 parts by weight of standard feed for poultry, pigs or ruminants.

The active substances are either mixed directly in with the carrier materials, or absorbed, after being dissolved in a suitable solvent, onto the carrier materials. The mixture is subsequently ground to the desired particle size of, for example, 5–10 microns. These feed premixes are mixed with 5800 parts by weight of standard feed, or are processed to give 6000 parts by weight of finished drinking liquid.

Furthermore, the final feed mixtures can be pelletised (feed pellets).

The active substances of the formula I or Ia according to the invention are added to the feed or to the drinking liquids for the animals, either directly or in the form of a premix, in amounts of 1 to 500 ppm, relative to the total amount of feed or drinking liquid.

Suitable premixes consist for example of a mixture of the active substance for instance with kaolin, limestone, aluminium oxide, ground shells, bolus alba, aerosol, starch or second flour, such as wheat second flour. A feed mixture is produced by thoroughly mixing the necessary amount of premix with the appropriate amount of a commercial standard feed.

What is claimed is:

1. A method for combatting harmful microorganisms which comprises administering to an animal infested with said microorganisms a microbicidally effective amount of a compound of the formula

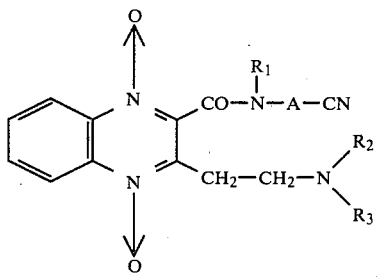

in which

R₁ is hydrogen or alkyl having 1 to 4 carbon atoms,
each of R₂ and R₃ is alkyl having 1 to 4 carbon atoms, or, together with the nitrogen atom to which they are attached, form a heterocyclic ring which is unsubstituted or substituted by alkyl having 1 to 4 carbon atoms and which has 4 or 5 ring carbon atoms and optionally an oxygen atom as a further hetero atom, and A is alkyl having 1 to 4 carbon atoms, or an acid addition salt thereof.

2. The method according to claim 1 in which the compound is

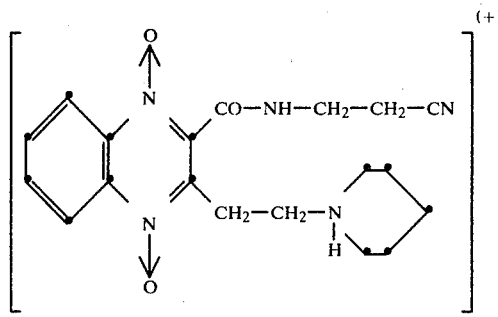

3. The method according to claim 1 in which the compound is

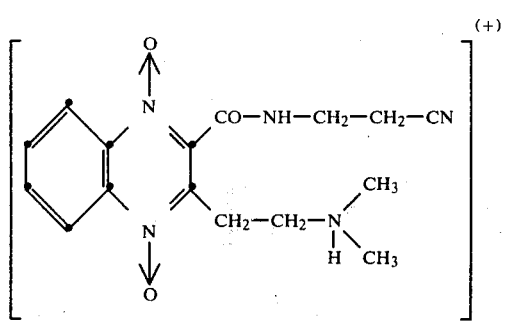

4. The method according to claim 1 in which the compound is

5. The method according to claim 1 in which the compound is

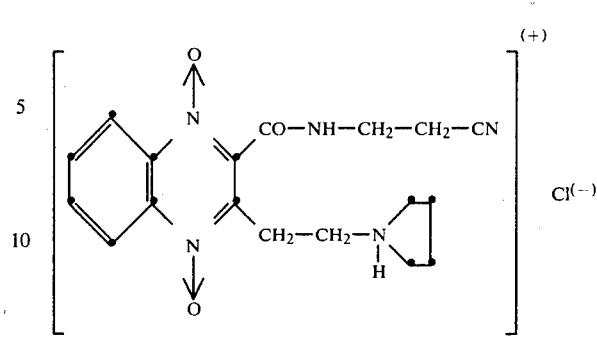

6. The method according to claim 1 in which the compound is

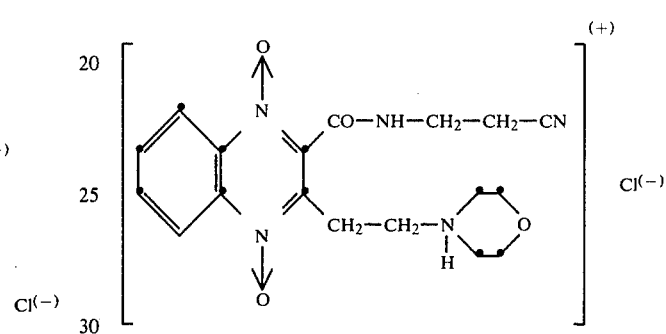

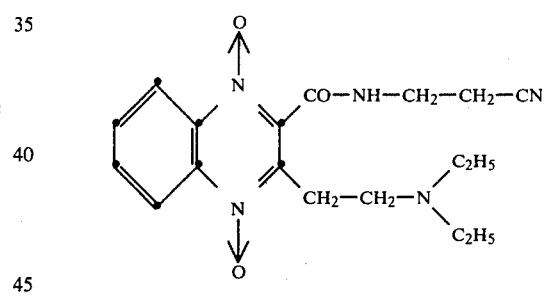

7. A method for combatting harmful microorganisms which comprises administering to an animal infested with said microorganisms a microbicidally effective amount of the compound of the formula

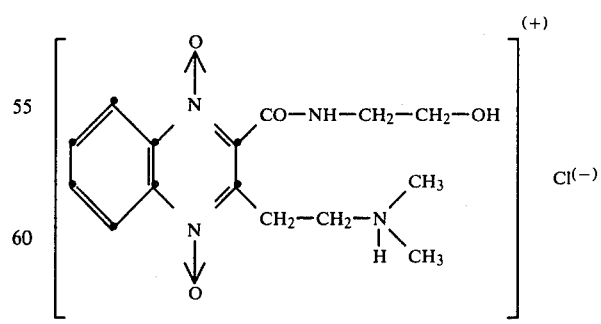

* * * * *